US00PP36802P2

(12) United States Plant Patent
Danziger

(10) Patent No.: US PP36,802 P2
(45) Date of Patent: Jul. 1, 2025

(54) ***HELIANTHUS* PLANT NAMED 'DHELSOSKBB'**

(50) Latin Name: *Helianthus annuus*
Varietal Denomination: DHELSOSKBB

(71) Applicant: Danziger "DAN" Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/967,915

(22) Filed: Dec. 4, 2024

(51) Int. Cl.
*A01H 5/02* (2018.01)
*A01H 6/14* (2018.01)

(52) U.S. Cl.
USPC ..... Plt./436

(58) Field of Classification Search
USPC ..... Plt./263.1, 436
See application file for complete search history.

(56) References Cited

U.S. PATENT DOCUMENTS

PP18,763 P2 * 4/2008 Hanson ..... A01H 6/14
Plt./437

* cited by examiner

*Primary Examiner* — Karen M Redden

(57) ABSTRACT

A new and distinct cultivar of *Helianthus* plant named 'DHELSOSKBB' is disclosed, characterized by large orange and yellow inflorescences. Plants are well-branched, vigorous, and have good longevity. The new variety is a *Helianthus*, normally produced as an outdoor garden or container plant.

2 Drawing Sheets

Figure 1:
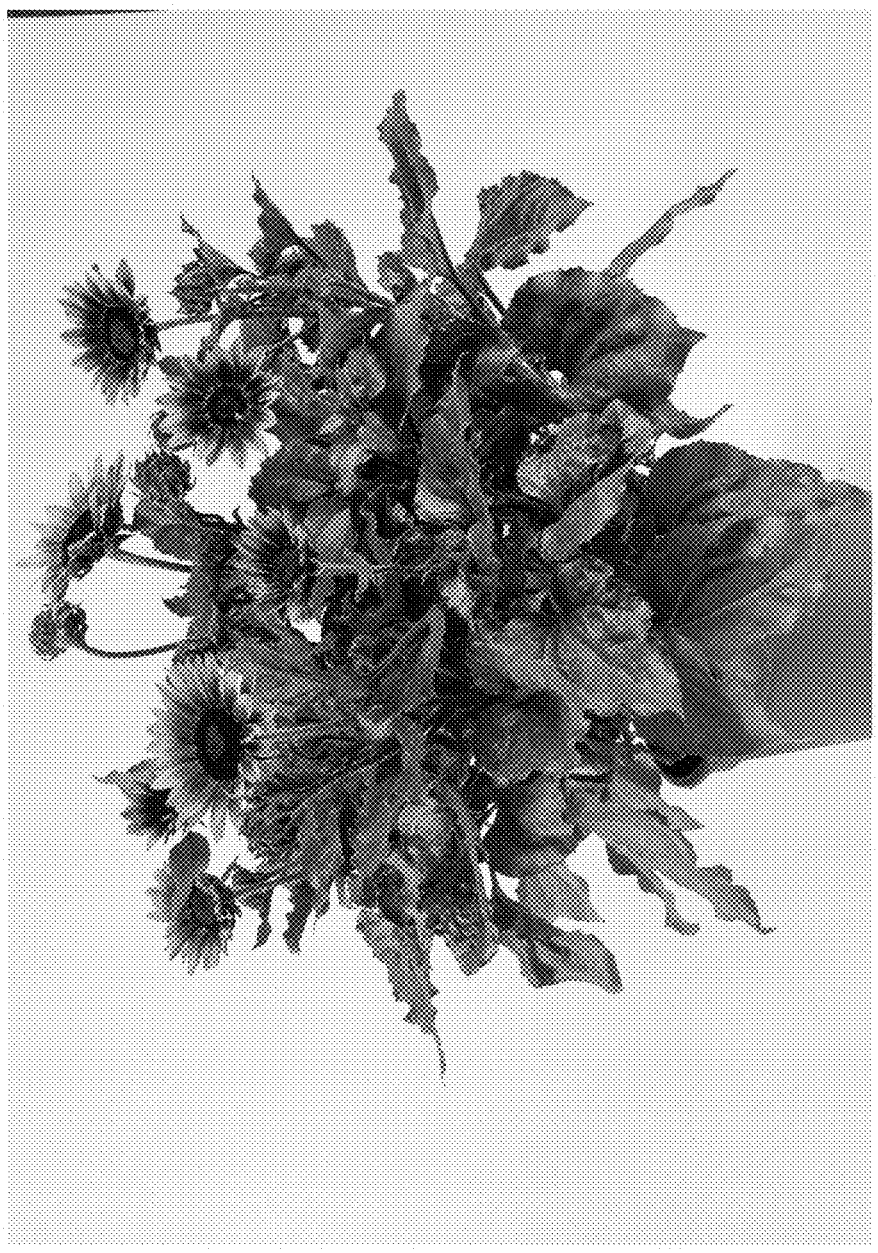

Latin name of the genus and species: *Helianthus annuus*.
Variety denomination: 'DHELSOSKBB'.

BACKGROUND OF THE INVENTION

The new *Helianthus* cultivar is a product of a planned breeding program conducted by the inventor, Gavriel Danziger in Moshav Mishmar Hashiva, Israel. The objective of the breeding program was to produce new *Helianthus* varieties for ornamental purposes. The seed parent is an unpatented internal *Helianthus* selection referred to as 'HLS-19-374'. The pollen parent is an unpatented internal *Helianthus* selection referred to as 'HLS-19-408'. The crossing resulting in this new variety was made in May 2019.

The new variety was found and selected in June 2020 by the inventor in a group of seedlings resulting from the crossing at the same nursery in Moshav Mishmar Hashiva, Israel.

Asexual reproduction of the new cultivar 'DHELSOSKBB' was first performed by terminal vegetative cuttings in June 2020, in Moshav Mishmar Hashiva, Israel. Subsequent propagation by vegetative cuttings has shown that the unique features of this cultivar are stable and reproduced true to type in more than 6 successive generations.

SUMMARY OF THE INVENTION

The cultivar 'DHELSOSKBB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHELSOSKBB' These characteristics in combination distinguish 'DHELSOSKBB' as a new and distinct *Helianthus* cultivar:

1. Well-branched plants.
2. Large inflorescences.
3. Moderate vigor.
4. Good longevity.

PARENT COMPARISONS

Plants of the new cultivar 'DHELSOSKBB' are similar to the seed parent in most horticultural characteristics; however, 'DHELSOSKBB' differs in the following:

1. Plants of the new variety are smaller than plants of the seed parent.
2. Plants of the new variety have more branches than plants of the seed parent.
3. Plants of the new variety have greater longevity than plants of the seed parent.
4. Leaves of the new variety are smaller than leaves of the seed parent.
5. Plants of the new variety produce more open inflorescences than plants of the seed parent.

Plants of the new cultivar 'DHELSOSKBB' are similar to the pollen parent in most horticultural characteristics; however, 'DHELSOSKBB' differs in the following:

1. Plants of the new variety are smaller than plants of the pollen parent.
2. Plants of the new variety have more branches than plants of the pollen parent.
3. Plants of the new variety have greater longevity than plants of the pollen parent.
4. Flower color of the new variety is orange and yellow, while the flower color of the pollen parent is yellow.

5. Plants of the new variety produce more open inflorescences than plants of the pollen parent.

COMMERCIAL COMPARISONS

Plants of the new cultivar 'DHELSOSKBB' can be compared to the commercial variety *Helianthus* 'Sol Seeker Bee Yellow', unpatented. These varieties are similar in most horticultural characteristics; however, 'DHELSOSKBB' differs in the following:

1. Plants of the new variety have greater longevity than plants of this comparator.
2. Plants of the new variety have more branches than plants of this comparator.
3. Plants of the new variety produce more open inflorescences than plants of this comparator.
3. Flower color of the new variety is orange and yellow, while the flower color of this comparator is yellow.
4. Inflorescences of the new variety are larger than inflorescences of this comparator.
5. Plants of the new variety are larger than plants of this comparator.

Plants of the new cultivar 'DHELSOSKBB' can also be compared to the commercial variety *Helianthus* 'Sol Seeker Golden Nectar', unpatented. These varieties are similar in most horticultural characteristics; however, 'DHELSOSKBB' differs in the following:

1. Plants of the new variety have greater longevity than plants of this comparator.
2. Plants of the new variety have more branches than plants of this comparator.
3. Plants of the new variety produce more open inflorescences than plants of this comparator.
4. Inflorescences of the new variety are larger than inflorescences of this comparator.
5. Plants of the new variety are larger than plants of this comparator.

BRIEF DESCRIPTION OF THE PHOTOGRAPHS

The accompanying photograph in FIG. 1 illustrates in full color a typical plant of 'DHELSOSKBB' grown in a 16 cm pot in Moshav Mishmar Hashiva, Israel under moderate Fall conditions.

Figure 2:
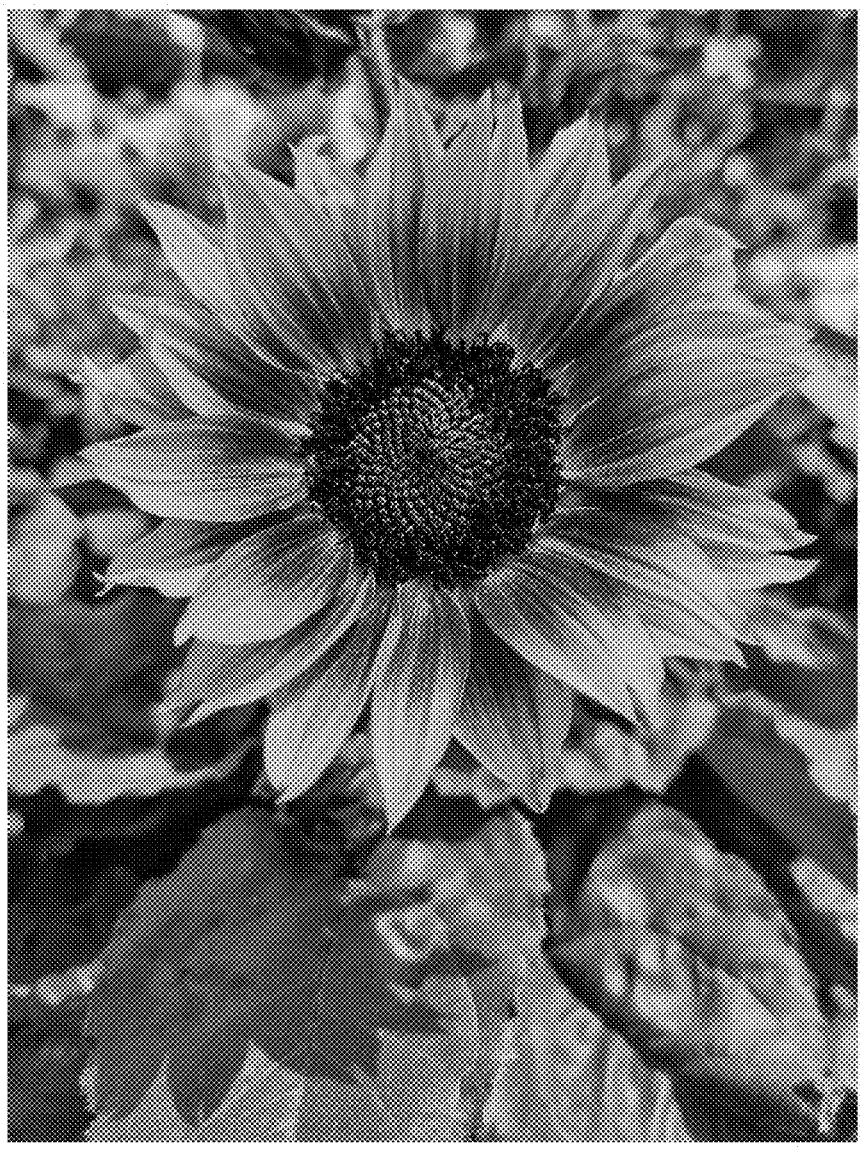

FIG. 2 illustrates in full color a close-up view of a typical flower of 'DHELSOSKBB' grown under the same moderate Fall conditions.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DHELSOSKBB' plants grown in a greenhouse in Moshav Mishmar Hashiva, Israel, under natural lighting. Measurements were taken during spring, summer, and autumn. The plants were approximately 45 days old from a rooted cutting in a 12 cm pot. The growing temperature ranged from approximately 24° C. to 32° C. during the day, 10° C. to 16° C. during the night. Measurements and numerical values represent averages of typical plant types.

Botanical classification: *Helianthus annuus* 'DHELSOSKBB'.

PROPAGATION

Total rooting time: 12 days at approximately 21° C.

Root description: Fine and fibrous. Brown to tan in color, not accurately measured with R.H.S. chart.

PLANT

Plant type: Herbaceous perennial.

Age of plant described: 45 days from a rooted cutting.

Pot size of plant described: 12 cm.

Height: About 30 cm to top of foliage; about 35 cm to top of flowering plane.

Plant spread: About 50 cm.

Vigor: Moderate.

Characteristics of primary branches:

*Diameter*.—Average 8 mm.

*Color*.—Near RHS Yellow-Green 144A, flushed Greyed-Purple 187A.

*Texture*.—Hirsute. Moderate density of hairs.

*Strength*.—Moderately strong.

FOLIAGE

Leaf:

*Arrangement*.—Sub-opposite.

*Attachment*.—Stalked.

*Quantity*.—Approximately 10 per lateral branch.

*Average length*.—9 to 10 cm, including petiole.

*Average width*.—3.5 to 4.5 cm.

*Shape of blade*.—Slightly asymmetrical ovate.

*Apex*.—Acute.

*Base*.—Rounded and somewhat oblique.

*Margin*.—Shallow dentate.

*Texture of top surface*.—Hirsute.

*Texture of bottom surface*.—Hirsute.

*Appearance of top surface*.—Matte.

*Appearance of bottom surface*.—Matte.

*Leaf internode length*.—Approximately 2.8 to 3.7 cm.

*Color*.—Young foliage upper side: Near RHS Green 137A. Young foliage under side: Near RHS Green 137B. Mature foliage upper side: Near RHS Yellow-Green 147A. Mature foliage under side: Near RHS Yellow-Green 147B.

*Venation*.—Type: Pinnate. Venation color upper side: Lateral veins near RHS Green 137A. Apical section of mid-vein near Yellow-Green 144C. Lower mid-vein near Greyed-Purple N186A. Venation color under side: Near RHS Yellow-Green 146D. Lowermost mid-vein flushed Greyed-Purple N186A.

Petiole:

*Length*.—2.0 to 3.0 cm.

*Diameter*.—2 to 3 mm.

*Color*.—Near RHS Greyed-Purple N186B.

*Texture*.—Hirsute.

FLOWER

Bloom period: Spring and summer.

Time to flowering from rooted cutting: About 6 weeks.

Inflorescence and flower type and habit: Terminal composite inflorescence.

Rate of flower opening: Approximately 2 weeks from bud to fully opened flower.

Flower longevity on plant: At least 1 to 2 weeks before any significant change is observed.

Approximate quantity of flowers per plant: Approximately 7 mature inflorescences, showing color and 10 immature, completely green inflorescences per plant.

Persistence: Persistent.

Inflorescence bud:

*Shape*.—Broad conical.

*Length*.—Approximately 2 cm.

*Diameter*.—Approximately 1.5 cm.

*Color*.—Near RHS Green 137A, turning Yellow 12A towards apex.

Inflorescence:

*Diameter*.—Approximately 10 cm.

*Depth*.—Approximately 5 cm.

*Disc diameter*.—Approximately 7 cm.

*Receptacle shape*.—Flattened.

*Receptacle height*.—Average 5 mm.

*Receptacle diameter*.—Average 1.5 cm.

*Receptacle color*.—Near RHS Yellow-Green 145C.

Individual flower bud:

*Shape*.—Broad conical.

*Length*.—Approximately 2 cm.

*Diameter*.—Approximately 1.5 cm.

*Color*.—Main color near RHS Green 137A, turning Yellow 12A towards apex.

Ray florets:

*Number*.—Average range 14 to 20.

*Length*.—Approximately 5 cm.

*Width*.—Approximately 1.4 cm.

*Shape*.—Linear.

*Margin*.—Entire.

*Texture*.—Smooth, all surfaces.

*Color*.—When opening: Upper surface: Near RHS Yellow 12A, lower approximate ⅓ near Greyed-Orange 172A. Lower surface: Near RHS Yellow 12B, lower approximate ⅓ flushed near Greyed-Orange 175D. Fully opened: Upper surface: Near RHS Yellow 12A, lower approximate ⅓ near Greyed-Orange 175B. Lower surface: Near RHS Yellow 12B, lower approximate ⅓ flushed near Greyed-Orange 175C.

Disc florets:

*Number*.—Average range 40 to 60.

*Length*.—Approximately 7 mm.

*Width*.—Approximately 7 mm.

*Shape*.—Linear.

*Margin*.—Entire.

*Texture*.—Pubescent.

*Color*.—When opening: Upper surface: Near RHS Brown 200A. Lower surface: Near RHS Yellow-Green 145D. Fully opened: Upper surface: Near RHS Brown 200A. Lower surface: Near RHS Yellow-Green 145D.

Phyllaries/involucral bracts:

*Quantity per inflorescence*.—Average 24, in 2 or 3 whorls.

*Shape*.—Apiculate.

*Length*.—Average range 1.4 to 2.0 cm.

*Width*.—Approximately 6 mm.

*Apex*.—Apiculate.

*Base*.—Tapered.

*Margin*.—Entire.

*Texture*.—Upper and lower surfaces coarsely pubescent.

*Color*.—Upper Surface: Near RHS Green 137A. Lower Surface: Near RHS Yellow-Green 145A.

Peduncle:

*Length*.—Average range 6 to 9 cm.

*Diameter*.—Approximately 3 mm.

*Color*.—Near RHS Yellow-Green 146C, flushed Greyed-Purple N186B.

REPRODUCTIVE ORGANS

Ray florets:

Stamens: None.

Anthers: None.

Pistil:

*Number*.—1.

*Length*.—Approximately 10 cm.

*Style*.—Length: Approximately 9 mm. Color: Near RHS Yellow 7D.

*Stigma*.—Shape: Linear. Color: Near RHS Yellow-Orange 21B.

Disc florets:

Stamens:

*Number*.—2, most commonly.

*Filament length*.—Approximately 1 mm.

Anthers:

*Length*.—Approximately 1 mm.

*Shape*.—Linear.

*Color*.—Near RHS Greyed-Purple N187D.

*Pollen*.—Not observed.

Pistil:

*Number*.—1.

*Length*.—Approximately 3 mm.

*Style*.—Length: Approximately 2 mm. Color: Near RHS Yellow-Green 154B, flushed Greyed-Purple N187D.

*Stigma*.—Shape: Linear. Color: Near RHS Yellow-Green 154B, flushed Greyed-Purple N187D.

OTHER CHARACTERISTICS

Disease resistance: Neither resistance nor susceptibility to additional normal diseases and pests of *Helianthus* has been observed.

Seed production:

*Shape*.—Oblong.

*Color*.—Dark brown.

*Size*.—Approximately 5 mm.

What is claimed is:

1. A new and distinct cultivar of *Helianthus* plant named 'DHELSOSKBB' as herein illustrated and described.

* * * * *